(12) United States Patent
Duan et al.

(10) Patent No.: US 10,738,039 B2
(45) Date of Patent: *Aug. 11, 2020

(54) METAL PLATING COMPOSITIONS

(71) Applicants: Dow Global Technologies LLC, Midland, MI (US); Rohm and Haas Electronic Materials LLC, Marlborough, MA (US)

(72) Inventors: Lingli Duan, Shanghai (CN); Chen Chen, Shanghai (CN); Shaoguang Feng, Shanghai (CN); Zukhra I. Niazimbetova, Westborough, MA (US); Maria Anna Rzeznik, Shrewsbury, MA (US)

(73) Assignees: Rohm and Haas Electronic Materials LLC, Marlborough, MA (US); Dow Global Technologies LLC, Midland, MI (US)

( * ) Notice: Subject to any disclaimer, the term of this patent is extended or adjusted under 35 U.S.C. 154(b) by 15 days.

This patent is subject to a terminal disclaimer.

(21) Appl. No.: 15/559,574

(22) PCT Filed: Apr. 28, 2015

(86) PCT No.: PCT/CN2015/077684
§ 371 (c)(1),
(2) Date: Sep. 19, 2017

(87) PCT Pub. No.: WO2016/172853
PCT Pub. Date: Nov. 3, 2016

(65) Prior Publication Data
US 2018/0051014 A1    Feb. 22, 2018

(51) Int. Cl.
*C07D 413/12*    (2006.01)
*C25D 3/38*    (2006.01)
*C07D 241/04*    (2006.01)
*C07D 265/33*    (2006.01)
*C07D 413/06*    (2006.01)
*C07D 413/10*    (2006.01)
*C25D 3/30*    (2006.01)

(52) U.S. Cl.
CPC .......... *C07D 413/12* (2013.01); *C07D 241/04* (2013.01); *C07D 265/33* (2013.01); *C07D 413/06* (2013.01); *C07D 413/10* (2013.01); *C25D 3/30* (2013.01); *C25D 3/38* (2013.01)

(58) Field of Classification Search
CPC .................................................. C07D 263/33
USPC ........................................................ 544/106
See application file for complete search history.

(56) References Cited

U.S. PATENT DOCUMENTS 10,106,512 B2 *  10/2018  Duan ................... C09D 179/08

OTHER PUBLICATIONS

Search report for corresponding China Application No. 201580078702.4 dated Jul. 1, 2019.
Jin, et al, "Synthesis of poly(cystine bisamide)-PEG block copolymers grafted with 1-(3-aminopropyl)imidazole and their phase transition behaviors", 2008, pp. 1558-1565, vol. 19.
Jin et al, "Synthesis of poly(cystine bisamide)-PEG block copolymers grafted with 1-(3-aminopropyl) imidazole and their phase tansition behaviors", Polymers for Advanced Technologies, Nov. 2008, pp. 1558-1565, vol. 19, No. 11.
Search report for corresponding European Application No. 15 89 0233 dated Oct. 16, 2018.
International search report for corresponding International Application No. PCT/CN2015/077684 dated Jan. 20, 2016.

* cited by examiner

*Primary Examiner* — Kahsay Habte
(74) *Attorney, Agent, or Firm* — John J. Piskorski

(57) ABSTRACT

Reaction products of diamines with the reaction products of monoamines and bisanhydrides are included as additives in metal electroplating baths. The metal electroplating baths have good throwing power and deposit metal layers having substantially planar surfaces. The metal plating baths may be used to deposit metal on substrates with surface features such as through-holes and vias.

1 Claim, No Drawings

METAL PLATING COMPOSITIONS

FIELD OF THE INVENTION

The present invention is directed to reaction products of diamines with reaction products of monoamines and bisanhydrides as additives for electroplating baths. More specifically, the present invention is directed to reaction products of diamines with reaction products of monoamines and bisanhydrides as additives for electroplating baths to provide electroplating baths which have good throwing power.

BACKGROUND OF THE INVENTION

Methods for electroplating articles with metal coatings generally involve passing a current between two electrodes in a plating solution where one of the electrodes is the article to be plated. A typical acid copper plating solution includes dissolved copper, usually copper sulfate, an acid electrolyte such as sulfuric acid in an amount sufficient to impart conductivity to the bath, a source of halide, and proprietary additives to improve the uniformity of the plating and the quality of the metal deposit. Such additives include levelers, accelerators and suppressors, among others.

Electrolytic copper plating solutions are used in a variety of industrial applications, such as decorative and anticorrosion coatings, as well as in the electronics industry, particularly for the fabrication of printed circuit boards and semiconductors. For circuit board fabrication, typically, copper is electroplated over selected portions of the surface of a printed circuit board, into blind vias and trenches and on the walls of through-holes passing between the surfaces of the circuit board base material. The exposed surfaces of blind vias, trenches and through-holes, i.e. the walls and the floor, are first made conductive, such as by electroless metal plating, before copper is electroplated on surfaces of these apertures. Plated through-holes provide a conductive pathway from one board surface to the other. Vias and trenches provide conductive pathways between circuit board inner layers. For semiconductor fabrication, copper is electroplated over a surface of a wafer containing a variety of features such as vias, trenches or combinations thereof. The vias and trenches are metallized to provide conductivity between various layers of the semiconductor device.

It is well known in certain areas of plating, such as in electroplating of printed circuit boards ("PCBs"), that the use of levelers in the electroplating bath can be crucial in achieving a uniform metal deposit on a substrate surface. Electroplating a substrate having irregular topography can pose difficulties. During electroplating a voltage drop typically occurs within apertures in a surface which can result in an uneven metal deposit between the surface and the apertures. Electroplating irregularities are exacerbated where the voltage drop is relatively extreme, that is, where the apertures are narrow and tall. Consequently, a metal layer of substantially uniform thickness is frequently a challenging step in the manufacture of electronic devices. Leveling agents are often used in copper plating baths to provide substantially uniform, or level, copper layers in electronic devices.

The trend of portability combined with increased functionality of electronic devices has driven the miniaturization of PCBs. Conventional multilayer PCBs with through-hole interconnects are not always a practical solution. Alternative approaches for high density interconnects have been developed, such as sequential build up technologies, which utilize blind vias. One of the objectives in processes that use blind vias is the maximizing of via filling while minimizing thickness variation in the copper deposit between the vias and the substrate surface. This is particularly challenging when the PCB contains both through-holes and blind vias.

Leveling agents are used in copper plating baths to level the deposit across the substrate surface and to improve the throwing power of the electroplating bath. Throwing power is defined as the ratio of the through-hole center copper deposit thickness to the copper thickness at the surface. Newer PCBs are being manufactured that contain both through-holes and blind vias. Current bath additives, in particular current leveling agents, do not always provide level copper deposits between the substrate surface and filled through-holes and blind vias. Via fill is characterized by the difference in height between the copper in the filled via and the surface. Accordingly, there remains a need in the art for leveling agents for use in metal electroplating baths for the manufacture of PCBs that provide level copper deposits while bolstering the throwing power of the bath.

SUMMARY OF THE INVENTION

A reaction product including one or more diamines including primary or secondary amine moieties with a reaction product including one or more monoamines including primary or secondary amine moieties and one or more compounds having formula:

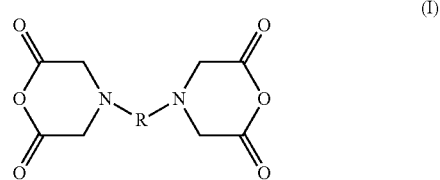

where R is a linking group.

Compositions include one or more sources of metal ions, an electrolyte and a reaction product including one or more diamines including primary or secondary amine moieties with a reaction product including one or more monoamines including primary or secondary amine moieties and one or more compounds having formula:

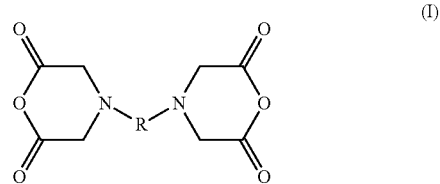

where R is a linking group.

Methods include providing a substrate; providing a composition including one or more sources of metal ions, an electrolyte and one or more reaction products including one or more diamines including primary or secondary amine moieties with a reaction product including one or more monoamines and one or more compounds having formula:

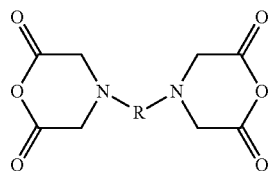

(I)

where R is a linking group; contacting the substrate with the composition; applying a current to the substrate; and plating a metal on the substrate.

The electroplating baths which include the reaction products provide substantially level metal layers across a substrate, even on substrates having small features and on substrates having a variety of feature sizes. The metal plating compositions have good throwing power and effectively deposit metals in blind vias and through-holes.

DETAILED DESCRIPTION OF THE INVENTION

As used throughout this specification the following abbreviations shall have the following meanings unless the context clearly indicates otherwise: A=amperes; $A/dm^2$=amperes per square decimeter=ASD; ° C.=degrees Centigrade; g=gram; mg=milligram; ppm=parts per million=mg/L; mol=moles; L=liter; μm=micron=micrometer; mm=millimeters; cm=centimeters; PO=propyleneoxide; EO=ethyleneoxide; DI=deionized; mL=milliliter; Mw=weight average molecular weight; and Mn=number average molecular weight; and v/v=volume to volume. All numerical ranges are inclusive and combinable in any order, except where it is clear that such numerical ranges are constrained to add up to 100%.

As used throughout the specification, "feature" refers to the geometries on a substrate. "Aperture" refers to recessed features including through-holes and blind vias. As used throughout this specification, the term "plating" refers to metal electroplating. "Deposition" and "plating" are used interchangeably throughout this specification. "Halide" refers to fluoride, chloride, bromide and iodide. "Monoamine" refers to an organic compound which has a single primary or secondary amine functional group available to react with anhydride. "Accelerator" refers to an organic additive that increases the plating rate of the electroplating bath and such accelerators may also function as brighteners. "Suppressor" refers to an organic additive that suppresses the plating rate of a metal during electroplating. "Leveler" refers to an organic compound that is capable of providing a substantially level or planar metal layer. The terms "leveler" and "leveling agent" are used interchangeably throughout this specification. The terms "printed circuit boards" and "printed wiring boards" are used interchangeably throughout this specification. The term "moiety" means a part of a molecule or polymer that may include either whole functional groups or parts of functional groups as substructures. The terms "moiety" and "group" are used interchangeably throughout the specification. The indefinite articles "a" and "an" refer to the singular and the plural.

One or more bisanhydrides having formula:

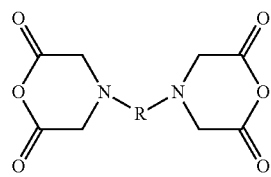

(I)

where R is a linking group joined by covalent bonds to the nitrogen of the anhydride rings are reacted with one or more monoamines including primary or secondary amine moieties to form a reaction product.

The linking groups R of formula (I) are organic moieties. Preferably R has the following structures:

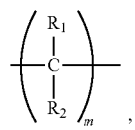

(II)

where $R_1$ and $R_2$ may be the same or different and include hydrogen, linear or branched ($C_1$-$C_4$)alkyl, hydroxyl, hydroxy($C_1$-$C_3$)alkyl, carboxyl, carboxy($C_1$-$C_3$)alkyl and ($C_1$-$C_3$)alkoxy, preferably, $R_1$ and $R_2$ include hydrogen or linear or branched ($C_1$-$C_4$), more preferably, $R_1$ and $R_2$ are hydrogen and m is an integer of 1 to 15, preferably from 2 to 10, more preferably from 2 to 3;

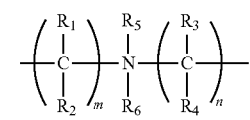

(III)

where $R_1$ and $R_2$ are defined as above; $R_3$ and $R_4$ may be the same or different and are the same groups as $R_1$ and $R_2$; $R_5$ and $R_6$ may be the same or different and include hydrogen, carboxyl and carboxy($C_1$-$C_3$)alkyl, preferably $R_5$ and $R_6$ mat be the same or different and are hydrogen and carboxyl; and m is as defined above and n is an integer of 1 to 15, preferably from 2 to 10, more preferably from 2 to 3 and preferably m and n are the same;

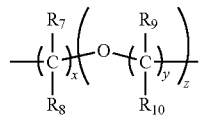

(IV)

where $R_7$, $R_8$, $R_9$ and $R_{10}$ may be the same or different and include hydrogen, linear or branched ($C_1$-$C_5$)alkyl, linear or branched hydroxy($C_1$-$C_5$)alkyl, carboxy($C_1$-$C_3$)alkyl, linear or branched($C_1$-$C_5$)alkoxy, preferably $R_7$, $R_8$, $R_9$ and $R_{10}$ may be the same or different and are hydrogen linear or branched ($C_1$-$C_5$)alkyl, more preferably $R_7$, $R_8$, $R_9$ and $R_{10}$ are hydrogen; x, y and z may be the same or different and are integers of 1 to 10, preferably from 2 to 3; and

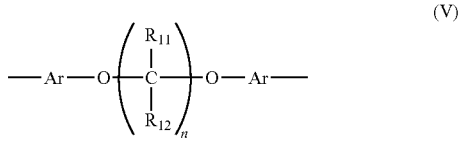

(V)

where $R_{11}$ and $R_{12}$ may be the same or different and are hydrogen or linear or branched $(C_1-C_5)$alkyl, preferably $R_{11}$ and $R_{12}$ are hydrogen, Ar is an aryl group having 5 to 6 carbon atoms, preferably 6 carbon atoms, more preferably R of formula (V) has the following structure: and n is as defined above.

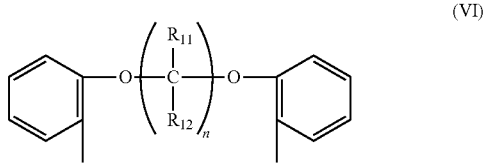

(VI)

and n is as defined above.

Monoamines include compounds having a general formula:

(VII)

where $R_{13}$ is hydrogen or linear or branched $(C_1-C_5)$alkyl, r is an integer of 0 to 10 with the proviso that when r is 0, R' is joined to the nitrogen atom by a covalent bond. Preferably $R_{13}$ is hydrogen. Preferably r is 1-4.

R' is a nitrogen containing moiety which may be linear or branched nitrogen containing groups, aromatic or non-aromatic heterocyclic groups. Linear or branched nitrogen containing moieties include, but are not limited to those having a general formula:

(VIII)

where $R_{14}$ and $R_{15}$ are independently linear or branched $(C_1-C_5)$alkyl and q is an integer of 1-10, preferably from 1 to 4.

Heterocyclic aromatic and non-aromatic nitrogen containing moieties include but are not limited to those derived from heterocyclic nitrogen compounds such as imidazoles, triazoles, tetrazoles, pyrazines, benzimidazoles, benzotriazoles, purines, piperazines, pyridazines, pyrazoles, triazines, tetrazines, pyrimidines, piperidines, benzoxazoles, oxazoles, pyridines, morpholines, pyrrolidines, pyrroles, quinolines, isoquinolines and benzothiazoles. The heterocyclic nitrogen moieties may have one or more substituent groups joined to the rings. Such substituent groups include, but are not limited to, linear or branched, substituted or unsubstituted alkyl, hydroxyl, nitro or nitroalkyl, nitroso or nitrosoalkyl, carbonyl, mercapto or mercaptoalkyl, linear or branched hydroxyalkyl, carboxyl, linear or branched carboxyalkyl, linear or branched alkoxy, substituted or unsubstituted aryl, linear or branched, substituted or unsubstituted arylalkyl, linear or branched, substituted or unsubstituted aminoalkyl, substituted or unsubstituted sulfonyl, linear or branched, substituted or unsubstituted amine. Also included are salts of the aromatic heterocyclic amines such as halogen salts.

Heterocyclic nitrogen moieties may have the following general structure:

(IX)

where $Q_1$-$Q_4$ may be nitrogen, oxygen, carbon, or sulfur with the proviso that only one of the $Q_1$-$Q_4$ may be oxygen or sulfur at any instance. Preferably, the ring has one to three nitrogen atoms, more preferably one or two nitrogen atoms. Most preferably, the ring is an imidazole. The nitrogen which joins the ring to a terminal carbon of formula (VII) above may have a positive charge where a counter anion is $X^-$ where $X^-$ is chloride, bromide, iodide, acetate, sulfate, hydroxyl, boron tetrafluoride or nitrate. The carbon atoms and nitrogen atoms may be substituted or unsubstituted. Substituents on carbon atoms and nitrogen atoms include but are not limited to, linear or branched, substituted or unsubstituted $(C_1-C_{10})$alkyl; hydroxyl; linear or branched alkoxy; linear or branched, substituted or unsubstituted hydroxy$(C_1-C_{10})$alkyl; linear or branched, substituted or unsubstituted alkoxy$(C_1-C_{10})$alkyl; linear or branched, substituted or unsubstituted carboxy$(C_1-C_{10})$alkyl; linear or branched, substituted or unsubstituted amino$(C_1-C_{10})$alkyl; substituted or unsubstituted aryl; linear or branched, substituted or unsubstituted aryl$(C_1-C_{10})$alkyl; substituted or unsubstituted sulfonyl; and substituted or unsubstituted amine.

Aromatic heterocyclic nitrogen moieties having fused rings may have the following general structure:

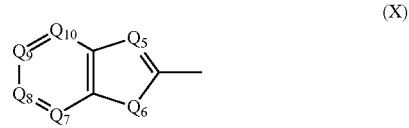

(X)

where $Q_5$-$Q_6$ may be carbon, oxygen, nitrogen or sulfur with the proviso that at least one of $Q_5$ and $Q_6$ is nitrogen and $Q_7$-$Q_{10}$ may be carbon or nitrogen atoms with the proviso that only two of $Q_7$-$Q_{10}$ may be nitrogen at the same instance. The carbon and nitrogen atoms of the rings may be substituted or unsubstituted. Substituents include but are not limited to, hydroxyl; linear or branched alkoxy; linear or branched, substituted or unsubstituted hydroxy$(C_1-C_{10})$ alkyl; linear or branched, substituted or unsubstituted alkoxy $(C_1-C_{10})$alkyl; linear or branched, substituted or unsubstituted carboxy$(C_1-C_{10})$alkyl; linear or branched, substituted or unsubstituted amino$(C_1-C_{10})$alkyl; substituted or unsubstituted aryl; linear or branched, substituted or unsubstituted aryl$(C_1-C_{10})$alkyl; substituted or unsubstituted sulfonyl; and substituted or unsubstituted amine. Such compounds include, but are not limited to, benzimidazoles, benzotriazoles, benzoxazoles, benzothiazoles, and purines. Preferably, such compounds are benzimidazoles.

Heterocyclic nitrogen compounds also include those having a general structure:

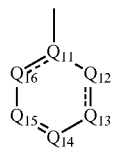
(XI)

where $Q_{11}$ may be nitrogen or carbon and $Q_{12}$-$Q_{16}$ may be nitrogen, carbon or oxygen with the proviso that at least one of $Q_{11}$-$Q_{16}$ is nitrogen and there are no more than four nitrogen atoms in the ring. The carbon atoms and nitrogen atoms in the ring may be substituted or unsubstituted. Substituent groups may be the same or different and include, but are not limited to, those substituent groups described for $Q_1$-$Q_{10}$, above. When $Q_{11}$ is nitrogen, the nitrogen may have a positive charge where a counter anion is $X^-$ and $X^-$ is as defined above. When oxygen is present in the ring, only one of $Q_{12}$-$Q_{16}$ is oxygen at any instance. Heterocyclic nitrogen compounds of structure (XI) may be aromatic or non-aromatic heterocyclic nitrogen compounds.

Preferred aromatic heterocyclic nitrogen containing R' moieties include those having the following formulae:

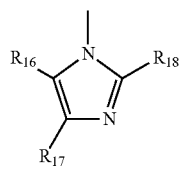
(XII)

where $R_{16}$, $R_{17}$ and $R_{18}$ are independently hydrogen, $(C_1$-$C_2)$alkyl or phenyl;

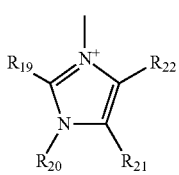
(XIII)

where $R_{19}$, $R_{20}$, $R_{21}$ and $R_{22}$ are independently hydrogen, $(C_1$-$C_2)$alkyl or phenyl and $X^-$ is as defined above;

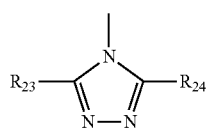
(XIV)

where $R_{23}$ and $R_{24}$ are independently hydrogen, $(C_1$-$C_2)$ alkyl or phenyl;

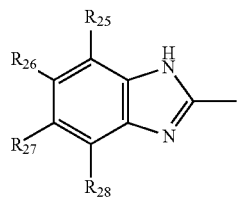
(XV)

where $R_{25}$, $R_{26}$, $R_{27}$ and $R_{28}$ are independently hydrogen, $(C_1$-$C_2)$alkyl or phenyl;

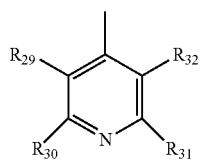
(XVI)

where $R_{29}$, $R_{30}$, $R_{31}$ and $R_{32}$ are independently hydrogen or $(C_1$-$C_2)$alkyl;

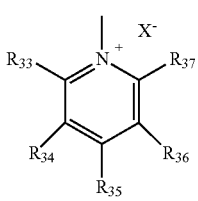
(XVII)

where $R_{33}$, $R_{34}$, $R_{35}$, $R_{36}$, $R_{37}$ and $X^-$ are independently hydrogen or $(C_1$-$C_2)$alkyl; and

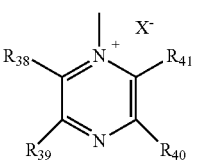
(XVIII)

where $R_{38}$, $R_{39}$, $R_{40}$, $R_{41}$ and $X^-$ are independently hydrogen or $(C_1$-$C_2)$alkyl above.

In general, the reaction products are prepared by mixing one or more bisanhydride compounds in an organic solvent, such as dimethylformamide (DMF), with stirring at room temperature. One or more diamines are then added dropwise to the mixture at room temperature with stirring for 8 to 15 hours. The diamines are added such that the molar ratio of diamines to anhydrides is 2:1. The product may be precipitated by adding anhydrous ethanol.

The reaction product may have a general formula:

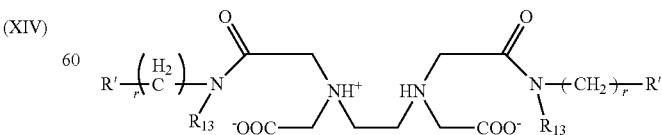
(XIX)

where R' and $R_{13}$ are as defined above.

One or more of the reaction products of the bisanhydrides and monoamines is then reacted with one or more diamines.

Diamines include compounds having a general formula:

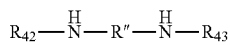
(XX)

where R″ is a linking group joined by covalent bonds to the terminal nitrogens. Such linking groups are organic moieties. Preferably R″ has the following structures:

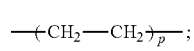
(XXI)

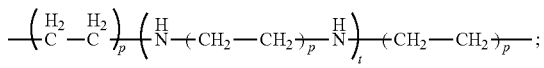
(XXII)

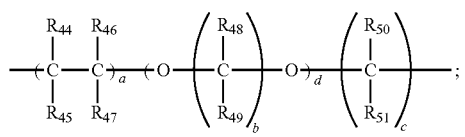
(XXIII)

a substituted or unsubstituted $(C_6-C_{18})$aryl;

(XXIV)

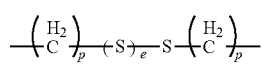
(XXV)

where $R_{42}$ and $R_{43}$ may be the same or different and include hydrogen, linear or branched $(C_1-C_{12})$alkyl, alkyleneoxy or substituted or unsubstituted $(C_6-C_{18})$aryl. Preferably, $R_{42}$ and $R_{43}$ are the same or different and are hydrogen, or linear or branched $(C_1-C_4)$alkyl. More preferably, $R_{42}$ and $R_{43}$ are hydrogen. Substituents on the aryl groups include, but are not limited to linear or branched $(C_1-C_{12})$alkyl, linear or branched hydroxy$(C_1-C_{12})$alkyl, hydroxyl, carboxyl, linear or branched carboxy$(C_1-C_{12})$alkyl, nitro group, mercapto group, linear or branched mercapto$(C_1-C_{12})$alkyl, linear or branched halo$(C_1-C_{12})$alkyl, preferably the aryl is a six membered ring, more preferably the aryl is an unsubstituted six membered ring; variables p and t may be the same or different and are independently integers of one or greater, preferably from 1 to 10, variable e is an integer of 0 to 3, preferably from 1 to 2, more preferably e is 1 and variables a, b, c and d may be the same or different and are numbers from 1 or greater, preferably from 1 to 10; when $R_{42}$ and $R_{43}$ are alkyleneoxy, the terminal carbons of the alkyleneoxy groups may be taken together to form a ring with the proviso that when $R_{42}$ and $R_{43}$ are joined together to form the ring, R' is also an alkyleneoxy group; $R_{44}-R_{51}$ may be the same or different and include hydrogen, linear or branched $(C_1-C_5)$ alkyl, linear or branched hydroxy$(C_1-C_5)$alkyl or linear or branched $(C_1-C_5)$alkoxy; and Z may be a carbon atom or nitrogen atom.

Diamines also include, but are not limited to, heterocyclic saturated non-aromatic compounds having the following formula:

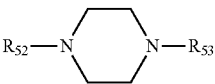
(XXVI)

where $R_{52}$ and $R_{53}$ may be the same or different and are hydrogen or amino$(C_1-C_{10})$alkyl, preferably $R_{52}$ and $R_{53}$ are hydrogen or amino$(C_1-C_3)$alkyl.

In general, the reaction products are prepared by mixing one or more of the reaction products of the bisanhydride compounds with the monoamine in an organic solvent, such as dimethylformamide (DMF), with stirring and heating or with stirring at room temperature. One or more diamines are then added dropwise to the mixture with heating and stirring. Heating is typically done in a range of 50° C. to 150° C. This mixture may then be heated for 2 hours to 15 hours followed by bringing the temperature down to room temperature with stirring. The product may be precipitated by adding anhydrous ethanol. The amounts reactants may vary but in general sufficient amount of each reactant is added to provide a product where the molar ratio of the product of the first reactant to the diamine reactant ranges from 1:0.1 to 1:2, preferably 1:0.5 to 1:2.

The plating composition and method are useful in providing a substantially level plated metal layer on a substrate, such as a printed circuit board. Also, the plating composition and method are useful in filling apertures in a substrate with metal. Also, the metal deposits have good throwing power.

Any substrate upon which metal can be electroplated is useful in the present invention. Such substrates include, but are not limited to: printed wiring boards, integrated circuits, semiconductor packages, lead frames and interconnects. An integrated circuit substrate may be a wafer used in a dual damascene manufacturing process. Such substrates typically contain a number of features, particularly apertures, having a variety of sizes. Through-holes in a PCB may have a variety of diameters, such as from 50 μm to 2 mm in diameter. Such through-holes may vary in depth, such as from 35 μm to 15 mm or greater. PCBs may contain blind vias having a wide variety of sizes, such as up to 200 μm diameter and 150 μm depth.

The metal plating compositions contain a source of metal ions, an electrolyte, and a leveling agent which is a reaction product as described above. The metal plating compositions may contain a source of halide ions, an accelerator and a suppressor. Metals which may be electroplated from the compositions include, but are not limited to: copper, tin and tin/copper alloys.

Suitable copper ion sources are copper salts and include without limitation: copper sulfate; copper halides such as copper chloride; copper acetate; copper nitrate; copper tetrafluoroborate; copper alkylsulfonates; copper arylsulfonates; copper sulfamate; copper perchlorate and copper gluconate. Exemplary copper alkylsulfonates include copper $(C_1-C_6)$alkylsulfonate and more preferably copper $(C_1-C_3)$ alkylsulfonate. Preferred copper alkylsulfonates are copper methanesulfonate, copper ethanesulfonate and copper propanesulfonate. Exemplary copper arylsulfonates include, without limitation, copper benzenesulfonate and copper p-toluene sulfonate. Mixtures of copper ion sources may be used. One or more salts of metal ions other than copper ions may be added to the present electroplating baths. Typically, the copper salt is present in an amount sufficient to provide an amount of copper metal of 10 to 400 g/L of plating solution.

Suitable tin compounds include, but are not limited to salts, such as tin halides, tin sulfates, tin alkane sulfonate such as tin methane sulfonate, tin aryl sulfonate such as tin benzenesulfonate and tin toluene sulfonate. The amount of tin compound in these electrolyte compositions is typically an amount that provides a tin content in the range of 5 to 150 g/L. Mixtures of tin compounds may be used in an amount as described above.

The electrolyte useful in the present invention may be alkaline or acidic. Typically the electrolyte is acidic. Suitable acidic electrolytes include, but are not limited to: sulfuric acid, acetic acid, fluoroboric acid, alkanesulfonic acids such as methanesulfonic acid, ethanesulfonic acid, propanesulfonic acid and trifluoromethane sulfonic acid, arylsulfonic acids such as benzenesulfonic acid and p-toluene sulfonic acid, sulfamic acid, hydrochloric acid, hydrobromic acid, perchloric acid, nitric acid, chromic acid and phosphoric acid. Mixtures of acids may be advantageously used in the present metal plating baths. Preferred acids include sulfuric acid, methanesulfonic acid, ethanesulfonic acid, propanesulfonic acid, hydrochloric acid and mixtures thereof. The acids may be present in an amount in the range of from 1 to 400 g/L. Electrolytes are generally commercially available from a variety of sources and may be used without further purification.

Such electrolytes may optionally contain a source of halide ions. Typically chloride ions are used. Exemplary chloride ion sources include copper chloride, tin chloride, sodium chloride and hydrochloric acid. A wide range of halide ion concentrations may be used in the present invention. Typically, the halide ion concentration is in the range of from 0 to 100 ppm based on the plating bath. Such halide ion sources are generally commercially available and may be used without further purification.

The plating compositions preferably contain an accelerator. Any accelerators (also referred to as brightening agents) are suitable for use in the present invention. Such accelerators are well-known to those skilled in the art. Accelerators include, but are not limited to, N,N-dimethyl-dithiocarbamic acid-(3-sulfopropyl)ester; 3-mercapto-propylsulfonic acid-(3-sulfopropyl)ester; 3-mercapto-propylsulfonic acid sodium salt; carbonic acid-dithio-o-ethylester-s-ester with 3-mercapto-1-propane sulfonic acid potassium salt; bis-sulfopropyl disulfide; bis-(sodium sulfopropyl)-disulfide; 3-(benzothiazolyl-s-thio)propyl sulfonic acid sodium salt; pyridinium propyl sulfobetaine; 1-sodium-3-mercaptopropane-1-sulfonate; N,N-dimethyl-dithiocarbamic acid-(3-sulfoethyl)ester; 3-mercapto-ethyl propylsulfonic acid-(3-sulfoethyl)ester; 3-mercapto-ethylsulfonic acid sodium salt; carbonic acid-dithio-o-ethylester-s-ester with 3-mercapto-1-ethane sulfonic acid potassium salt; bis-sulfoethyl disulfide; 3-(benzothiazolyl-s-thio)ethyl sulfonic acid sodium salt; pyridinium ethyl sulfobetaine; and 1-sodium-3-mercaptoethane-1-sulfonate. Accelerators may be used in a variety of amounts. In general, accelerators are used in an amount of 0.1 ppm to 1000 ppm. Preferably, the accelerator concentration is in the range of 0.5 ppm to 100 ppm. More preferably, the accelerator concentration is in the range of 0.5 ppm to 50 ppm, and most preferably, in the range of 0.5 ppm to 25 ppm.

Any compound capable of suppressing the metal plating rate may be used as a suppressor in the present electroplating compositions. Suitable suppressors include, but are not limited to, polypropylene glycol copolymers and polyethylene glycol copolymers, including ethylene oxide-propylene oxide ("EO/PO") copolymers and butyl alcohol-ethylene oxide-propylene oxide copolymers. Suitable butyl alcohol-ethylene oxide-propylene oxide copolymers are those having a weight average molecular weight of 100 to 100,000, preferably 500 to 10,000. When such suppressors are used, they are typically present in an amount in the range of from 1 to 10,000 ppm based on the weight of the composition, and more typically from 5 to 10,000 ppm.

In general, the reaction products have a number average molecular weight (Mn) of 200 to 10,000, typically from 300 to 50,000, preferably from 500 to 8000, although reaction products having other Mn values may be used. Such reaction products may have a weight average molecular weight (Mw) value in the range of 1000 to 50,000, typically from 5000 to 30,000, although other Mw values may be used.

The amount of the reaction product (leveling agent) used in the metal electroplating compositions depends upon the particular leveling agents selected, the concentration of the metal ions in the electroplating composition, the particular electrolyte used, the concentration of the electrolyte and the current density applied. In general, the total amount of the leveling agent in the electroplating composition ranges from 0.01 ppm to 5,000 ppm based on the total weight of the plating composition, although greater or lesser amounts may be used. Preferably, the total amount of the leveling agent is from 0.1 to 1000 ppm, more preferably, from 0.1 to 500 ppm, most preferably, from 0.1 to 100 ppm. In addition to their leveling activity, the reaction products may also function as suppressors.

The electroplating compositions may be prepared by combining the components in any order. It is preferred that the inorganic components such as source of metal ions, water, electrolyte and optional halide ion source are first added to the bath vessel followed by the organic components such as leveling agent, accelerator, suppressor, and any other organic component.

The electroplating compositions may optionally contain two or more leveling agents. Such additional leveling agents may be another leveling agent of the present invention, or alternatively, may be any conventional leveling agent. Suitable conventional leveling agents that can be used in combination with the present leveling agents include, without limitations, those disclosed in U.S. Pat. No. 6,610,192 to Step et al., U.S. Pat. No. 7,128,822 to Wang et al., U.S. Pat. No. 7,374,652 to Hayashi et al. and 6,800,188 to Hagiwara et al. Such combination of leveling agents may be used to tailor the characteristics of the plating bath, including leveling ability and throwing power.

Typically, the plating compositions may be used at any temperature from 10 to 65° C. or higher. Preferably, the temperature of the plating composition is from 10 to 35° C. and more preferably, from 15 to 30° C.

In general, the metal electroplating compositions are agitated during use. Any suitable agitation method may be used and such methods are well-known in the art. Suitable agitation methods include, but are not limited to air sparging, work piece agitation, and impingement.

Typically, a substrate is electroplated by contacting the substrate with the plating composition. The substrate typically functions as the cathode. The plating composition contains an anode, which may be soluble or insoluble. Potential is typically applied to the electrodes. Sufficient current density is applied and plating performed for a period of time sufficient to deposit a metal layer having a desired thickness on the substrate as well as fill blind vias, trenches and through-holes or to conformally plate through-holes. Current densities include, but are not limited to, the range of 0.05 to 10 A/dm$^2$, although higher and lower current densities may be used. The specific current density depends in part upon the substrate to be plated, the composition of the plating bath and the desired surface metal thickness. Such current density choice is within the abilities of those skilled in the art.

An advantage of the present invention is that substantially level metal deposits are obtained on a PCB and other substrates. By "substantially level" metal layer is meant that the step height, i.e., the difference between areas of dense very small apertures and areas free of or substantially free of apertures, is less than 5 μm, and preferably, less than 1 μm. Through-holes and/or blind vias in the PCB are substantially filled. A further advantage of the present invention is that a wide range of apertures and aperture sizes may be filled.

Throwing power is defined as the ratio of the average thickness of the metal plated in the center of a through-hole compared to the average thickness of the metal plated at the surface of the PCB sample and is reported as a percentage. The higher the throwing power, the better the plating composition is able to conformally plate the through-hole.

The compounds provide metal layers having a substantially level surface across a substrate, even on substrates having small features and on substrates having a variety of feature sizes. The plating methods effectively deposit metals in through-holes and blind via holes such that the metal plating compositions have good throwing power and reduced cracking.

While the methods of the present invention have been generally described with reference to printed circuit board manufacture, it is appreciated that the present invention may be useful in any electrolytic process where an essentially level or planar metal deposit and filled or conformally plated apertures are desired. Such processes include, but are not limited to semiconductor packaging and interconnect manufacture as well as plating on plastics.

The following examples are intended to further illustrate the invention but are not intended to limit its scope.

EXAMPLE 1

In step 1, ethylenediaminetetraacetic (EDTA) bisanhydride (10 mmoles) was dissolved in 30 mL of dimethylformamide (DMF) and 20 mmoles of 1H-imidazole-1-propylamine (structure A) was dissolved in 30 mL of DMF. The EDTA bisanhydride solution was added into the 1H-imidazole-1-propylamine solution dropwise for 12 hours at room temperature. The reaction product was precipitated by adding 60 mL of anhydrous ethanol, then washed with acetone and dried under a vacuum. The reaction product included an inner salt as shown by structure (B).

In step 2, 10 mmoles of the reaction product of step 1 and 10 mmoles of hexamethylenediamine (C) were mixed at room temperature. Then the mixture was heated at 145° C. for 6 hours under a nitrogen atmosphere. The final product (D) was used without further purification.

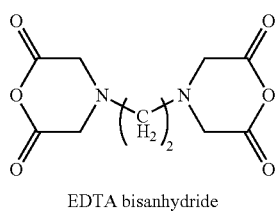

EDTA bisanhydride

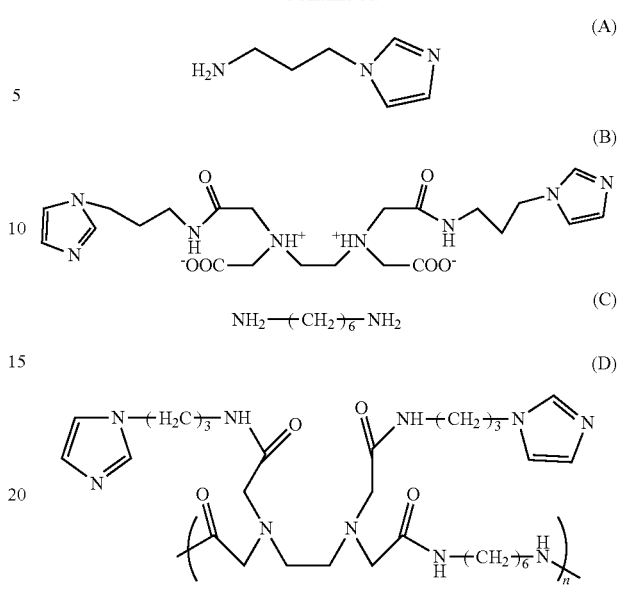

EXAMPLE 2

Three aqueous acid copper electroplating baths having the basic formulation disclosed in Table 1 below were prepared.

TABLE 1

| COMPONENT | AMOUNT |
| --- | --- |
| Purified copper sulfate pentahydrate | 73 g/L |
| Sulfuric acid | 235 g/L |
| Chloride ions as hydrogen chloride | 60 ppm |
| EO/PO copolymer with a Mw <5000 (suppressor) | 1.5 g/L |
| Disulfide compound having sulfonic acid with a Mw <1000 (accelerator) | 10 ppm |

The pH of the baths was less than 1. Each bath included the final reaction product, polymer D, of Example 1 above as a leveler. The brightener was bis(sodium-sulfopropyl)disulfide. The amount and type of leveler and brightener included in each bath is disclosed in Table 2 below.

Test panels 3.3 mm thick with average through-hole diameters of 300 μm were immersed in the aqueous acid copper electroplating baths. Copper plating was done for 80 minutes at 25° C. The current was 2.16 ASD. The copper plated samples were analyzed to determine the throwing power ("TP") of the plating bath, and percent cracking according to the following methods.

Throwing power was calculated by determining the ratio of the average thickness of the metal plated in the center of a through-hole compared to the average thickness of the metal plated at the surface of the test panel. The throwing power is reported in Table 2 as a percentage.

Cracking was determined according to the industry standard procedure, IPC-TM-650-2.6.8. Thermal Stress, Plated-Through Holes, published by IPC (Northbrook, Ill., USA), dated May, 2004, revision E.

TABLE 2

| LEVELER (ppm) | BRIGHTENER (PPM) | TP % | CRACK % |
|---|---|---|---|
| 0.5 | 1 | 55.7 | 100 |
| 1 | 1 | 54.3 | 100 |
| 0.5 | 3 | 51.3 | 100 |

Although cracking was high, the copper electroplating baths which included reaction product D from Example 1 had improved throwing power.

EXAMPLE 3

In step 1, EDTA bisanhydride (10 mmoles) is dissolved in 30 mL of dimethylformamide (DMF) and 20 mmoles of the benzimidazole-2-propylamine compound of structure A' is dissolved in 30 mL of DMF. The EDTA bisanhydride solution is added into the benzimidazole-2-propylamine solution dropwise for 12 hours at room temperature. The reaction product is precipitated by adding 60 mL of anhydrous ethanol, then washing with acetone and drying under a vacuum. The reaction product includes an inner salt as shown by structure (B').

In step 2, 10 mmoles of the reaction product of step 1 and 10 mmoles of hexamethylenediamine (C) are mixed at room temperature. Then the mixture is heated at 145° C. for 6 hours under a nitrogen atmosphere. The final product (D') is used without further purification.

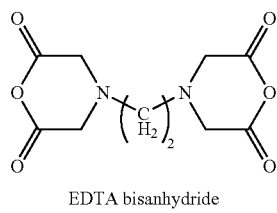

EDTA bisanhydride (A')

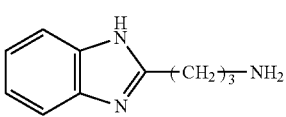

(B')

(C)

$NH_2$—$(CH_2)_6$—$NH_2$ (D')

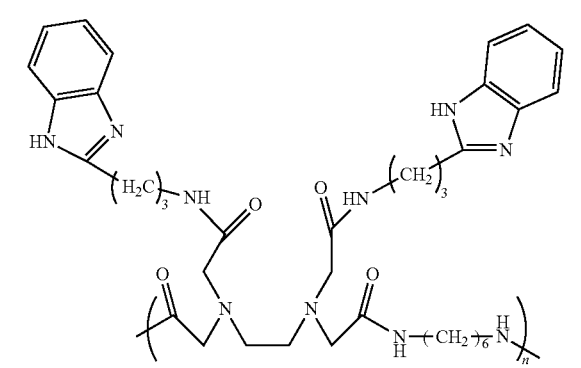

The reaction product, compound D' above, is expected to provide a copper electroplating bath having good throwing power.

What is claimed is:

1. A composition comprising one or more sources of metal ions chosen from copper salts and tin salts, an electrolyte and a reaction product of one or more diamines with a reaction product of one or more monoamines and one or more compounds having formula:

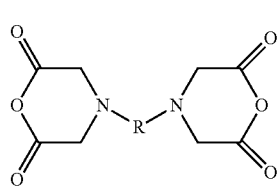

(I)

where R is a linking group comprising:

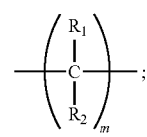

(II)

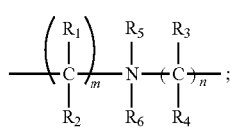

(III)

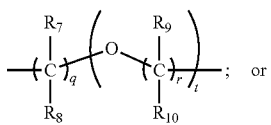

(IV)

or

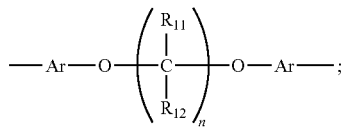

(V)

where $R_1$, $R_2$, $R_3$ and $R_4$ may be the same or different and comprise hydrogen, linear or branched $(C_1-C_4)$alkyl, hydroxyl, hydroxy$(C_1-C_3)$alkyl, carboxyl, carboxy$(C_1-C_3)$alkyl or $(C_1-C_3)$alkoxy; $R_5$ and $R_6$ may be the same or different and comprise hydrogen, carboxyl and carboxy$(C_1-C_3)$alkyl; $R_7$, $R_8$, $R_9$ and $R_{10}$ may be the same or different and comprise hydrogen, linear or branched $(C_1-C_5)$alkyl, linear or branched hydroxy$(C_1-C_5)$alkyl, carboxy$(C_1-C_3)$alkyl, linear or branched$(C_1-C_5)$ alkoxy; $R_{11}$ and $R_{12}$ may be the same or different and comprise hydrogen or linear or branched $(C_1-C_5)$alkyl, Ar is an aryl group having 5 to 6 carbon atoms; n and m may be the same or different and are integers of 1 to 15; and q, r and t may be the same or different are integers of 1 to 10; and wherein the one or more monoamines comprises a formula:

(VII)

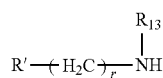

wherein $R_{13}$ is hydrogen or linear or branched $(C_1$-$C_5)$ alkyl, R' is a nitrogen containing moiety comprising linear or branched nitrogen containing groups, aromatic or non-aromatic heterocyclic groups and r is 0 to 10 with a the proviso that when r is 0, R' is joined to the nitrogen atom by a covalent bond; and wherein the one or more diamines have the formula:

(XX)

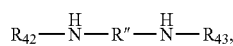

or (XXVI)

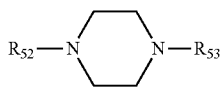

where $R_{42}$ and $R_{43}$ may be the same or different and comprise hydrogen, linear or branched $(C_1$-$C_{12})$alkyl, alkyleneoxy or substituted or unsubstituted $(C_6$-$C_{18})$ aryl, and R" comprises:

$-(CH_2-CH_2)_p-$;  (XXI)

$-(\overset{H_2}{C}-\overset{H_2}{C})_p-(\overset{H}{N}-(CH_2-CH_2)_p-\overset{H}{N})_t-(CH_2-CH_2)_p-$;  (XXII)

(XXIII)

$-(\overset{R_{44}}{\underset{R_{45}}{C}}-\overset{R_{46}}{\underset{R_{47}}{C}})_a-O-(\overset{R_{48}}{\underset{R_{49}}{C}})_b-O)_d-(\overset{R_{50}}{\underset{R_{51}}{C}})_c-$;

$-(H_2C)_p-Z\langle\rangle Z-(CH_2)_p-$;  (XXIV)

$-(\overset{H_2}{C})_p-(S)_e-S-(\overset{H_2}{C})_p-$;  (XXV)

or
a substituted or unsubstituted $(C_6$-$C_{18})$aryl; where $R_{44}$-$R_{51}$ may be the same or different and comprise hydrogen, linear or branched $(C_1$-$C_5)$alkyl, linear or branched hydroxy$(C_1$-$C_5)$alkyl or linear or branched $(C_1$-$C_5)$ alkoxy; and Z is a carbon atom or nitrogen atom; and p and t may be the same or different and are independently integers of one or greater, e is an integer of 0 to 3, and a, b, c and d may be the same or different and are numbers from 1 or greater, and wherein $R_{52}$ and $R_{53}$ may be the same or different and are hydrogen or amino$(C_1$-$C_{10})$alky.

* * * * *